United States Patent [19]

Leonard et al.

[11] Patent Number: 5,079,337

[45] Date of Patent: Jan. 7, 1992

[54] MACROMOLECULAR CONJUGATES OF HEMOGLOBIN, A PROCEDURE FOR THEIR PREPARATION AND THEIR USES

[75] Inventors: Michèle Leonard, Vandoeuvre; Edith Dellacherie, Malzeville; Jean M. L. Neel, Villers-Lès-Nancy; Claude Vigneron, Nancy; Pierre Labrude, Laxou, all of France

[73] Assignee: Pasteur Merieux Serums et Vaccins S.A., Lyon, France

[21] Appl. No.: 159,582

[22] PCT Filed: Jul. 2, 1987

[86] PCT No.: PCT/FR87/00262

§ 371 Date: Feb. 3, 1988

§ 102(e) Date: Feb. 3, 1988

[87] PCT Pub. No.: WO88/00055

PCT Pub. Date: Jan. 14, 1988

[30] Foreign Application Priority Data

Jul. 2, 1986 [FR] France ............... 86 09625

[51] Int. Cl.$^5$ ............ C07K 15/22; A61K 37/14
[52] U.S. Cl. ........................ 530/385; 525/54.1
[58] Field of Search ................ 530/385; 514/6; 424/101; 525/54.1

[56] References Cited

U.S. PATENT DOCUMENTS

| | | | |
|---|---|---|---|
| 4,064,118 | 12/1977 | Wong | 530/385 |
| 4,377,512 | 3/1983 | Ajisaha et al. | 530/385 |
| 4,412,989 | 11/1983 | Iwashita et al. | 530/385 |
| 4,529,719 | 7/1985 | Tye | 514/6 |
| 4,698,387 | 10/1987 | Schmidt et al. | 514/6 |
| 4,710,488 | 12/1987 | Wong | 514/6 |
| 4,777,244 | 10/1988 | Banhard et al. | 530/385 |
| 4,920,194 | 4/1990 | Feller et al. | 530/385 |

FOREIGN PATENT DOCUMENTS

| | | |
|---|---|---|
| 0043675 | 1/1982 | European Pat. Off. |
| 0067029 | 12/1982 | European Pat. Off. |
| 0142125 | 5/1985 | European Pat. Off. |
| 2328478 | 5/1977 | France |
| 2551660 | 3/1985 | France |

OTHER PUBLICATIONS

Dellacherie et al, *Chemical Abstracts*, vol. 100, No. 8, p. 318, 56721m (1984).
Sacco et al, *Chemical Abstracts*, vol. 104, No. 331, 20264 lm (Jun. 9, 1986).

*Primary Examiner*—Howard E. Schain
*Assistant Examiner*—Susan M. Perkins
*Attorney, Agent, or Firm*—Fleit, Jacobson, Cohn, Price, Holman & Stern

[57] ABSTRACT

The subject of the invention is a water-soluble macromolecular conjugate of hemoglobin characterized in that it is constituted
on the one hand, by hemoglobin,
on the other, by a water-soluble polymer P containing polar groups, this macromolecular conjugate contains Z sites, bound to the polymer P and containing at least one negative charge carried for example by sulfate groups, the polymer P being bound to hemoglobin
on the one hand, through the intermediary of at least one linkage established between at least one of the Z sites contained in the polymer and hemoglobin,
and, on the other, through the intermediary of at least one covalent linkage established between the polymer and hemoglobin, or between at least one of the Z sites contained in the polymer and hemoglobin.

The macromolecular conjugates according to the invention exhibit a lower affinity for oxygen than that of free hemoglobin.

29 Claims, 6 Drawing Sheets

MACROMOLECULAR CONJUGATES OF HEMOGLOBIN, A PROCEDURE FOR THEIR PREPARATION AND THEIR USES

The invention relates to new, macromolecular conjugates, a procedure for their preparation and their uses as transporters of oxygen, particularly in the context of transfusions.

It is known that the intravenous injection of an aqueous solution of hemoglobin free of stroma and made isotonic with blood is possible. However, one of the disadvantages experienced with hemoglobin is that it does not remain in the circulation but diffuses outside of the vascular system, in particular on account of its small size.

Several procedures have been used to counteract this disadvantage, i.e. to enhance the intravascular persistence of free hemoglobin in the framework of its use as blood "substitute" or as filling solute acting as a transporter of oxygen.

For example, hemoglobin has been coupled to water-soluble macromolecules which have been rendered non-toxic, non-antigenic and hemocompatible. In this way many examples of hemoglobins modified by being chemically linked to water-soluble polymers have shown that the time during which hemoglobin resides in the organism can be considerably increased.

Among the various polymers used, the most common are the polysaccharides and, in particular, dextran (French patent No. 2.328.478), hydroxyethyl-starch (French patent No. 2.238.478), inulin (European patent application No. 43.675), and polyalkylene glycols, more especially polyethylene glycols.

However, in all of these cases the hemoglobin thus modified by being directly linked to these polymers possesses oxygen-carrying properties which are poorly suited to their use in blood transfusion.

In fact, it will be recalled that a blood substitute can only play a role equivalent to that fulfilled by native hemoglobin in the interior of erythrocytes to the extent that the adduct that it forms with oxygen is reversible, i.e. that it is capable of binding oxygen (the hemoglobin is then in the oxygenated form) but also that it is capable of easily releasing the oxygen (the hemoglobin is then in the deoxygenated form).

This property with respect to oxygen is characterized by the curve (called the Barcroft curve) which represents the variation in the amount of oxygen bound per unit mass of the transporter as a function of the partial pressure of oxygen contained in the atmosphere to which the hemoglobin is exposed.

In the case of an aqueous solution of native hemoglobin (concentration 15 $\mu$moles/liter) at pH 7.2 and 25° C. this variation is represented by the reference plot shown in FIG. 1.

One of the parameters associated with this curve is the half-saturation pressure ($P_{50}$) which is the partial pressure of oxygen to which the solution of hemoglobin must be subjected for it to absorb an amount of oxygen equivalent to 50% of the maximal amount with which it is capable of combining. Now in the case of modified hemoglobin (hemoglobin coupled to polymers) as indicated above, the curve in FIG. 1 (dashed line) showing the percentage of oxygen combined with the hemoglobin at given partial pressures of oxygen is shifted to the left with respect to the curve representing native hemoglobin (continuous line).

This means that the pressure $P_{50}$ of the modified hemoglobin is lower than that of native hemoglobin; in other words, the modified hemoglobin shows too strong an affinity for oxygen with the disadvantage that the oxygen cannot be returned rapidly to the irrigated tissues.

This change in the oxygen-carrying properties of the modified hemoglobin can be explained in particular by the following reasons:

inside the red cell native hemoglobin is subject to the influence of 2,3-diphosphoglycerate (2,3-DPG) which is the naturally occurring intraerythrocytic effector which binds to the amine groups at the allosteric site of deoxyhemoglobin, leading to a lowering of the affinity of hemoglobin for oxygen.

Improvements to counteract this disadvantage have been suggested in which the coupling between the polymers and the hemoglobin is carried out in the presence of temporary effectors (or ligands) such as 2,3-diphosphoglycerate or inositol hexaphosphate and in the total absence of oxygen (French patent No. 83.145.45).

These polyphosphates complex strongly to the allosteric site of deoxyhemoglobin, thus stabilizing it and protecting the amino groups which are essential for the process of oxygen transport.

However, these effectors are eliminated either during the purification steps of the hemoglobin-polymer conjugates or, if the purification steps have not led to the removal of the effectors, under the dissociating conditions existing in the plasma.

It has been suggested that recourse be had to permanent effectors, for example by coupling pyridoxal-5'-phosphate (Japan Kokai Tokyo JP No. 59.104.323) to counteract this disadvantage.

The use has also been suggested of ligands containing several phosphate groups which, after being bound to hemoglobin, markedly diminish its affinity for oxygen.

However, one of the disadvantages presented by these substances is that their preparation requires at least two, and usually several, operations to be carried out on the hemoglobin and this circumstance leads to the formation of degradation products, in particular methemoglobin.

It has also been suggested in the European patent application No. 142,125 that hemoglobin/polymer-ligand ionic complexes be used, prepared, on the one hand, from addition compounds formed between ligands and water-soluble polymers and, on the other, from hemoglobin, the linkage between the ligand-polymer addition compounds and hemoglobin being an ionic linkage.

Such complexes are capable of reducing the affinity of hemoglobin for oxygen.

However, the purely ionic association between hemoglobin and the ligand-polymer addition compounds is only sufficiently strong when hemoglobin is present in the deoxygenated form, a circumstance which implies that when the hemoglobin is reoxygenated the ligand-polymer addition compounds are ejected from the phosphate binding site of hemoglobin and there is no longer any strong ionic interaction between the above-mentioned addition compounds and hemoglobin.

If such ionic complexes are injected into the organism, it is to be expected that the ligand-polymer addition compound, which is not linked strongly or specifically with hemoglobin, will be rapidly eliminated from the organism, particularly if its molecular mass is not very large, and that the hemoglobin escapes from the circulation.

The aim of the invention is to find a solution for these disadvantages by suggesting new macromolecular conjugates of hemoglobin, the size of which is such that their extravascular diffusion tendency is limited or even reduced to zero, which are protected from the dissociating conditions of the plasma, the oxygen-carrying properties of which are not impaired but enhanced compared with those of free hemoglobin, and the preparation of which entails a limited number of reaction steps on hemoglobin.

These features have been realized by the new macromolecular conjugates of the invention.

One of the features of the invention is to furnish new macromolecular conjugates which are physiologically compatible and capable of binding oxygen reversibly.

Another feature of the invention is to furnish new macromolecular conjugates which are capable of releasing oxygen more readily than free hemoglobin.

Another feature of the invention is to suggest new macromolecular conjugates which are easy to synthesize on an industrial scale.

A further feature of the invention is to furnish new macromolecular conjugates of hemoglobin prepared by making use of a procedure in which hemoglobin is subjected to not more than two reaction steps and usually to only one.

Yet another feature of the invention is to suggest novel aqueous solutions containing new macromolecular conjugates of hemoglobin which can be used as substitutes for blood, particularly in operations requiring transfusions or the perfusion of an organ.

Another feature of the invention is to furnish solutions of hemoglobin, the oxygen-carrying properties of which are characterized by an increase of the $P_{50}$ in vitro compared with free hemoglobin and which remains stable in vivo.

Another feature of the invention is to suggest new macromolecular conjugates of hemoglobin exhibiting at one and the same time a moderate affinity for oxygen and a high hydrodynamic volume, which leads to an enhancement of the intravascular persistence of hemoglobin by suppressing hemoglobinuria during transfusion studies.

The new macromolecular conjugates of hemoglobin according to the invention exhibiting an affinity for oxygen which is lower than that of free hemoglobin are characterized in that they are constituted on the one hand, by hemoglobin, which can change from the deoxygenated form to the oxygenated form in a reversible manner, and on the other, by a water-soluble polymer P, non-toxic, preferably non-antigenic, hemocompatible, of molecular mass varying from about 1,000 to about 500,000, preferably from about 1,000 to about 100,000, and which bears polar groups, preferably hydroxyl, carboxyl or amino groups, this macromolecular conjugate contains Z sites linked to the polymer P and includes at least one negative charge borne by anionic groups, constituted by sulfate, and/or phosphate and/or carboxylate residues, the polymer P is linked to hemoglobin on the one hand through the intermediary of at least one ionic bond between at least one of the Z sites contained in the polymer and hemoglobin, and on the other, through the intermediary of at least one covalent bond formed either between the polymer and hemoglobin or between one of the Z sites contained in the polymer and hemoglobin, the number of covalent links between the polymer and hemoglobin is such that the macromolecular conjugate has an average molecular mass varying from about 70,000 to about 1,000,000, and preferably from about 70,000 to about 500,000, the relationship between the negative charge, the number of sites and the number of monomers is the following:

when each site contains a unique anionic group constituted by a sulfate or a phosphate residue, there is at least one site for every ten monomers of the polymer, when at least one of the sites contains at least two anionic groups, constituted by sulfate and/or phosphate residues, there is at least one site per polymer, when each site contains negative charges derived from carboxylate residues, at least two carboxylate groups must be present at the same Z site and at least one Z site must exist for every five monomers, when at least one of the sites contains at least three negative charges derived from carboxylate residues, there is at least one site per polymer.

It has been noted that a necessary condition of the macromolecular conjugates of the invention being water-soluble, devoid of toxicity and preferably non-antigenic, and hemocompatible is that the polymers P, which are used to form part of the above-mentioned macromolecular conjugates are water-soluble, devoid of toxicity and preferably non-antigenic, and hemocompatible.

It has been noted that the presence in the chain of the polymer of Z sites, bearers of anionic groups which play the role of permanent effectors, increases the partial pressure at which 50% of the hemoglobin in solution is oxygenated, an increase which cannot be attributed to the possible existence of free ligands.

These permanent effectors are such that they also enable the hemoglobin molecule to pass reversibly from the deoxygenated form to the oxygenated form but which confer greater stabilization on the confirmation of the hemoglobin molecule in the deoxygenated form, a property which leads to a diminution of the affinity of hemoglobin for oxygen. In other words, the effectors enable hemoglobin to transport oxygen reversibly and, in particular, to return the oxygen readily to the tissues which are being irrigated.

The covalent linkage is such that it confers on the macromolecular conjugate of the invention a stability making it non-biodegradable, or only slightly so, in the plasma throughout the period during which the macromolecular conjugate must exercise its oxygen-carrying functions, i.e. 2 to 3 days, a property which prevents the external or extravascular diffusion of the hemoglobin.

In the macromolecular conjugates of the invention the hemoglobin is linked to the polymer by at least one ionic bond but, in addition, by covalent links between the polymers and hemoglobin, the number of which is critical in order to avoid in particular the phenomenon of intermolecular cross-linking which is detrimental to the properties of hemoglobin.

This critical number of covalent links reflects the fact that the mean molecular weight of the macromolecular conjugates of the invention must not exceed about 1,000,000.

The distribution of the density of the negative charge must be sufficient for an ionic bond to be formed with the amino groups at the allosteric site of hemoglobin, i.e. the site of the naturally occurring effector in erythrocytes, 2,3-diphosphoglycerate.

It has been observed that statistically one sulfate or phosphate group for every ten monomers is necessary and sufficient but this ratio may be higher than 1/10.

It has also been noted that when at least one of the sites contains at least two anionic groups constituted by phosphate and/or sulfate ions, then a single site suffices for the entire polymer chain, a circumstance which does not exclude the possibility of having several sites on the same chain.

In the case in which the negative charge density is constituted by carboxylate groups, it is necessary for there to be at least two carboxylate ions at the same site and a site comprising two carboxylate ions is necessary for every five monomers. It has been observed that when at least three carboxylate ions are present, the charge density of the site is such that one site is sufficient for the polymer chain, an observation which does not exclude the possibility of having several sites on the same chain.

The polymers which constitute part of the macromolecular conjugates of the invention which are degraded in the plasma have a mean molecular weight varying from about 1,000 to 500,000.

The polymers which constitute part of the macromolecular conjugates of the invention and which are not degraded in the organism must have a mean molecular weight equal to, or less than about 10,000, since above this value it is difficult for the polymers to pass the renal barrier and they thus accumulate in the organism. This is particularly the case for the polyalkylene glycols, polyvinylpyrrolidone, polymethacrylate and certain polysaccharides which, since they are not biodegradable, must possess a mean molecular weight equal to, or lower than about 10,000.

The polymers which constitute part of the macromolecular conjugates of the invention must be used over a molecular weight range in which they are preferably non-antigenic. Thus, in the case of dextran, its molecular weight must be less than about 70,000.

DETAILED DESCRIPTION OF THE INVENTION

Figure 1:
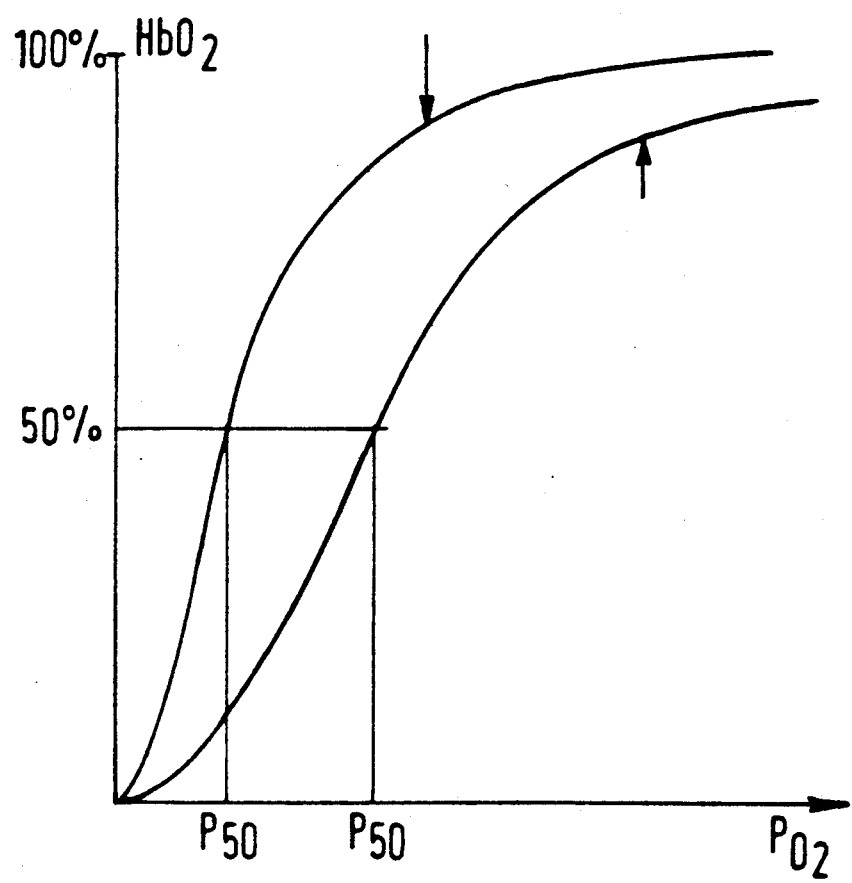
FIG. 1 shows the Barcroft curve of natural hemoglobin and modified hemoglobin of the prior art.

According to an attractive embodiment of the invention, the internal salt bridges between the $NH_3^+$ groups and the $COO^-$ groups of hemoglobin remain intact when hemoglobin is in the deoxygenated form. By salt bridges are meant certain intramolecular bonds which form between $NH_3^+$ ions and $COO^-$ anions when hemoglobin is in the deoxygenated form.

The salt bridges in the macromolecular conjugates of the invention must preferably remain intact since if the ions which participate in the formation of these salt bridges are involved in other linkages, the transition of hemoglobin from the oxygenated form to the deoxygenated form occurs with very great difficulty and is incomplete.

The expression "intact salt bridges" means that at least 50% of the salt bridges have not been disrupted and that advantageously 80% to 90% or even 100%, of the salt bridges have not been disrupted.

The criteria used to verify whether the salt bridges are intact are, in particular, the following:

a) The affinity curve for oxygen:
If the affinity curve for oxygen (Barcroft curve) is displaced to the right with respect to that of free hemoglobin this implies that the salt bridges have not been modified.

b) Hill coefficient (n):
This parameter is an expression for the sigmoidal shape of the Barcroft curve and reflects the degree of cooperativity in the binding of oxygen. The value of n makes it possible to estimate the permanence of the allosteric behaviour of hemoglobin. In the case of native hemoglobin, this coefficient lies between 2.7 and 3.0.

c) Bohr effect:
It consists of determining the oxygen-carrying behaviour of hemoglobin at different pHs which enables the perturbation accompanying the different reaction steps to be evaluated.

According to another attractive embodiment of the invention the macromolecular conjugates of the invention are chosen from among the polysaccharides, in particular among the hydroxyalkyl starches, the alkyl group of which contains 2 to 4 carbon atoms, inulin, dextran and its derivatives, in particular aminated dextran, polyvinyl alcohol, polyvinylpyrrolidone, polymethacrylate and its derivatives, polypeptides, the polyalkylene glycols in which the alkene group contains from 2 to 5 carbon atoms, in particular polyethylene glycol and polypropylene glycol.

According to another attractive embodiment of the invention Z represents $OSO_3H$.

According to another attractive embodiment of the invention Z is derived from pyridoxal sulfate, epinephrine disulfate, epinephrine trisulfate, norepinephrine disulfate, norepinephrine trisulfate and phenolphthalein disulfate.

According to another attractive embodiment of the invention Z represents $OPO_3H_2$.

According to another attractive embodiment of the invention Z is derived from pyridoxal phosphate, adenosine triphosphate, phosphotyrosine, phosphoserine, inositol hexaphosphate and its derivatives, inositol tri-, tetra-, pentaphosphate and their derivatives.

According to another useful embodiment of the invention Z is derived from

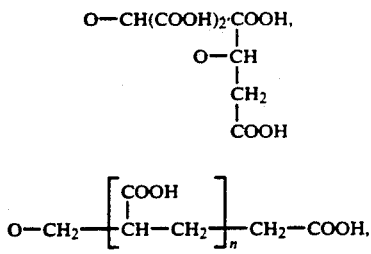

n varying from 1 to 4.

According to another useful embodiment of the invention Z is derived from a polycarboxylic acid containing from about 2 to about 10 carbon atoms in the main chain, a benzene carboxylic acid containing at least 2 carboxylic acid functions, 2,3-diphosphoglycerate, citric acid, 1,2,3-propane tricarboxylate or butane tetracarboxylate.

According to another useful embodiment of the invention Z is derived from 2-hydroxy 5-formyl phosphoserine benzamide corresponding to the formula:

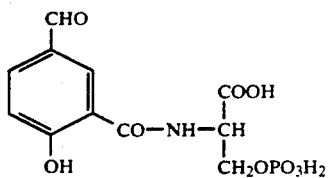

or 4-formyl phosphoserine benzamide corresponding to formula:

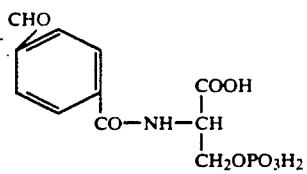

According to another useful embodiment of the invention the Z site comprises at least three functional groups which are such that
one of the functions is a function through which the Z group is linked to the polymer,
one of the functions is a sulfate, phosphate or carboxylate function capable of establishing an ionic bond with an amine at the allosteric site of hemoglobin,
one of the functions is an aldehyde, carboxylic acid or OH function capable of forming a covalent link with a $NH_2$ group of hemoglobin.

The nature of the bond which links Z to the polymer depends on the reactive species present and on the conditions of the reaction. The linkages through which Z is bound to the polymer are ether, ester, amide or amine linkages.

As an illustration, an ester linkage is obtained by the action of $H_2SO_4$ or $H_3PO_4$ (after binding $H_2SO_4$ generates the $-OSO_3H$ site and $H_3PO_4$ gives rise to $-O-PO_3H_2$) on the polymer; an ether linkage is established by a radical reaction with acrylic acid or by the action of chlorosuccinic acid on the OH groups of the polymers. an amide linkage is formed by reaction between the carboxylate residues of the Z groups and the $NH_2$ groups of the polymers; an amine linkage is produced by reaction between the aldehyde residues of the Z groups and the $NH_2$ groups of the polymers, followed by reduction. These last two reactions may be carried out simultaneously, i.e. reductive amination.

The covalent linkages between the polymer and hemoglobin are established between the $NH_2$ groups of hemoglobin and the carboxylic acid, aldehyde or hydroxyl groups which exist either on the polymer or at the Z sites.

The linkage between the polymer and hemoglobin is an amide, imine amine or carbamate linkage.

According to one embodiment of the invention the covalent linkages are established directly between the aldehyde, carboxylic acid or hydroxyl groups of the polymers and the $NH_2$ groups of hemoglobin.

According to another useful embodiment of the invention the covalent linkages are established between the aldehyde, carboxylic acid or hydroxyl residues of the Z groups attached to the polymers and the $NH_2$ groups of hemoglobin.

According to a particularly attractive embodiment of the invention the covalent linkages are established between the carboxyl groups and the $NH_2$ groups of hemoglobin.

Advantageous macromolecular conjugates of hemoglobin according to the invention are those in which the polymer is constituted by dextran, preferably having a mean molecular weight of about 40,000 and preferably containing about 5.4 moles of $OSO_3H$ groups per 10 moles of glucopyranose and the covalent linkages between the polymer and hemoglobin arise from coupling between aldehyde groups previously formed on the dextran, preferably in a ratio of about 18 aldehyde groups for every 100 glucosidic units, and $NH_2$ groups of hemoglobin.

Advantageous macromolecular conjugates of hemoglobin according to the invention are those in which the polymer is constituted by dextran, preferably with a mean molecular weight of about 10,000 and containing about 9.8 moles of $OSO_3H$ groups per 10 units of glucopyranose and the covalent linkages between the polymer and hemoglobin arise from coupling between aldehyde groups previously formed on the dextran, preferably in a ratio of about 14 aldehyde groups per 100 glucosidic units, and $NH_2$ groups of hemoglobin.

Other advantageous macromolecular conjugates of hemoglobin according to the invention are those in which the polymer is constituted by dextran, preferably with a mean molecular weight of about 6,000 and containing about 1.7 sulfate ions per 10 units of glucopyranose and the covalent linkages between the polymer and hemoglobin result from linkages between aldehyde groups previously formed on the dextran, preferably in a ratio of about 18 aldehyde groups per 100 glucosidic units, and $NH_2$ groups of hemoglobin.

Other advantageous macromolecular conjugates of hemoglobin according to the invention are those in which the polymer is constituted by dextran, preferably with a mean molecular weight of about 40,000 and containing about 12 moles of $OPO_3H_2$ groups per 10 moles of glucopyranose and the covalent linkages between the polymer and hemoglobin result from linkages between aldehyde groups previously formed on the dextran, preferably in a ratio of about 18 aldehyde groups per 100 glucosidic units, and $NH_2$ groups of hemoglobin.

Other advantageous macromolecular conjugates of hemoglobin according to the invention are those in which the polymer is constituted by aminated dextran, preferably with a mean molecular weight of about 40,000, the ionic linkages being established through carboxylic acid groups of the benzene hexacarboxylic acid residue bound to the polymer and the covalent linkages being formed between the carboxylic acid groups of benzene hexacarboxylic acid not involved in the ionic linkages defined above and $NH_2$ groups of hemoglobin.

Other advantageous macromolecular conjugates of hemoglobin according to the invention are those in which the polymer is constituted by polycarboxylated dextran, preferably with a mean molecular weight of about 40,000 and containing on average about one dicarboxylic acid chain per monomer, and the covalent linkages are formed through the carboxylic acid groups not involved in ionic linkage with hemoglobin and $NH_2$ groups of hemoglobin.

In order to prepare the macromolecular conjugates of hemoglobin of the invention, it is possible
- in the first step to couple the Z groups to the polymer either by converting the polymer P beforehand into a polyol, if this is necessary, then by coupling the Z groups by known methods,
- or by using a compound Z-Y in which Y is a reactive or activatable function such as aldehyde, carboxylic acid, amine, hydroxyl, halogen, for example, chlorine, with the aid of an appropriate reagent,
- or by coupling the Z groups to the polymer P by means of a radical reaction,
- then in the second step the polymer P bearing the Z group is made to react with hemoglobin in an aqueous medium at a pH lying between about 5 and about 9, conditions under which hemoglobin is not denatured, in order to form simultaneously covalent and ionic linkages between the polymer and hemoglobin.

The first step of the preparation of the macromolecular conjugates of the invention, which consists in coupling the Z groups to the polymer, can be carried out by known methods, for example sulfatation, phosphorylation or carboxymethylation of the polymer P in the form of a polyol. In the case in which the polymer P is not a polyol, it is necessary to transform it beforehand into a polyol.

The first step of the preparation of the macromolecular conjugates of the invention can also be carried out by using compounds of the type Z-Y in which Y is an aldehyde, carboxylic acid, amine, hydroxyl or halogen function. These compounds Z-Y are used by having recourse to standard chemical methods; for example, a penta- or hexacarboxylic acid, 2,3-diphosphoglycerate acid or pyridoxal-5'-phosphate can be coupled to a polymer which has previously been polyaminated.

In this case it is imperative to remove all traces of the compound Z-Y, for example by desalting on a gel filtration column. In fact, the presence of unreacted compound Z-Y must be avoided since its contamination of the macromolecular conjugates of the invention even at low concentrations can lead to false conclusions regarding the properties of the conjugates of the invention.

Recourse may also be had to any other method enabling polyanionic chains to be attached to a polymer such as a method of radiochemical grafting.

The second step mentioned above is one involving reaction between the polymer and hemoglobin and, if necessary, may be preceded by a step in which the polymer is activated before it is allowed to react with hemoglobin; however, this activation may be carried out almost simultaneously with the reaction between the polymer and hemoglobin.

During the second step the polymer reacts with hemoglobin resulting on the one hand, in the establishment of the ionic linkages between the Z sites of the polymer and hemoglobin and, on the other, in the formation of the covalent linkages between the polymer and hemoglobin.

In this second step, reaction occurs through
- either the carboxylic acid, aldehyde or hydroxyl functions of the Z sites,
- or the carboxylic acid, aldehyde or hydroxyl functions of the polymer.

In the case in which reaction occurs between carboxylic acid groups and $NH_2$ groups of hemoglobin, the carboxylic acid groups can be activated by the reagents commonly used in peptide synthesis such as the water-soluble carbodiimides, in particular the hydrochloride of 1-ethyl-3-3-dimethylaminopropyl) carbodiimide (EDCI), N-hydroxysuccinimide or N-ethoxycarbonyl-2-ethoxy-1,2-dihydroquinoline (EEDQ).

The linkage formed is thus an amide linkage.

In the case in which it is the aldehyde groups which enter into reaction with $NH_2$ groups of hemoglobin, recourse may be had to reductive amination for example. Reductive amination consists of the condensation of an aldehyde with an amine to form an imine and in the simultaneous reduction of the imine to an amine by means of a reducing agent such as $NaBH_4$, $NaCNBH_3$, dimethylaminoborane or HCOOH.

The linkage thus formed is an amine linkage.

In the case in which it is aldehyde groups which are made to react with $NH_2$ groups of hemoglobin, conditions may be used such that the linkage obtained is an imine linkage which must subsequently be stabilized by reduction to an amine by means of a mild reducing agent such as one of those mentioned above.

When neither the Z groups nor the polymer P possess aldehyde or carboxylic acid groups but contain hydroxyl groups, some of which are attached to adjacent carbon atoms, aldehyde groups may be formed on the polymer P by, for example, periodate oxidation of the latter, in particular by means of $NaIO_4$. The linkage formed between these aldehyde groups and the amino groups of hemoglobin is thus an imine linkage which must be stabilized by reduction to an amine, for example with $NaBH_4$.

When neither the Z sites nor the polymer P possesses aldehyde or carboxylic acid groups, the polymer containing OH groups can be made to react with $NH_2$ groups of hemoglobin by means of an appropriate reagent such as cyanogen bromide or carbonyldiimidazole. In this case, the linkage formed is a carbamate linkage.

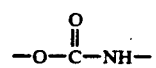

The macromolecular conjugates of hemoglobin in which the covalent linkages between the polymer and hemoglobin are imine linkages are not stable in the organism, and it is for this reason that it is appropriate to stabilize the imine function by reducing it to an amine function using $NaBH_4$, $NaCNBH_3$ or dimethylaminoborane.

The macromolecular conjugates of hemoglobin in which the covalent linkages are of the imine type are new intermediates which can be used as reagents, particularly in vitro.

In the case in which it is necessary to stabilize the covalent linkages, hemoglobin is not subjected to more than two reaction steps and in the other cases, whether polymer P is activated or not, hemoglobin itself is subjected to a single reaction step, a circumstance which is particularly advantageous since a limited number of reaction steps carried out on hemoglobin (two at most) is one of the essential conditions if hemoglobin is not to be denatured and the yield of the reaction is not to be impaired.

During the second step it is in fact essential that hemoglobin is not subjected to either serious denaturation or to an appreciable reduction of the relative mobility of the various parts of the molecule in order to preserve, at least in part, its oxygen-carrying properties.

The second step of the reaction is carried out in aqueous medium, buffered for unbuffered, at a pH of between 5 and 9, possibly in the presence of an activating agent as indicated above, in the absence of oxygen, for a period of time sufficient for reaction to occur but too short for significant amounts of methemoglobin to have formed (higher than about 5%) and at a temperature at which hemoglobin is not denatured.

The aqueous medium is buffered by standard buffers in order to stabilize the pH at the desired value.

The duration of the reaction varies from about 30 min to about 20 h and advantageously lasts about 1 h to about 8 h at a temperature varying between about 3° and about 30° C.

The duration of the reaction depends particularly on the temperature at which reaction is carried out.

The hemoglobin used is in the deoxygenated form and it is advantageous to use a 9% hemoglobin solution.

The ratio of the molar concentrations of polymer and hemoglobin must, in addition, be such that the large majority of the hemoglobin molecules become covalently linked to the polyanionic polymer.

As an example, it may be pointed out that by allowing a mixture of dextran polymer, the mean molecular weight of which lies between about 10,000 and about 40,000, and hemoglobin to react at a temperature varying from about 3° to 30° C. in solution in an aqueous medium at a pH close to 6.5 and at a ratio of the molar concentrations of dextran to hemoglobin which varies from about 0.5 to about 2, macromolecular conjugates of the invention are obtained which, on examination by gel permeation chromatography for example, reveal no trace of free hemoglobin.

The macromolecular conjugates of the invention possess the advantage of being easy to synthesize, with little or no formation of methemoglobin (less than about 5%) and the synthesis involves a limited number of reactions on hemoglobin which thus prevents its denaturation.

Moreover, the macromolecular conjugates of the invention do not contain unbound effectors of low molecular weight which lead to an increase of the $P_{50}$ in vitro experiments but which can easily be removed by extrarenal or extravascular diffusion during assays in vivo, thus rapidly abolishing their effect.

The macromolecular conjugates of the invention possess the advantage of exhibiting only a moderate affinity for oxygen and of having a high hydrodynamic volume which increases the intravascular persistence of hemoglobin during transfusion operations by suppressing hemoglobinuria.

The conjugates of hemoglobin irreversibly bound to polyanionic polymers prepared according to the invention can act as blood substitutes when they are dissolved in aqueous solutions of appropriate composition, particularly in operations requiring transfusions or the perfusion of an organ.

Consequently, the invention also relates to aqueous solutions containing the conjugates described above and in particular solutions made isotonic with blood by prolonged dialysis against a Tyrode solution (composition: NaCl 8 g/l; KCl 0.2 g/l; $CaCl_2$ 0.2 g/l; $MgCl_2$ 0.1 g/l; $NaH_2PO_4$ 0.05 g/l; $NaHCO_3$ 1 g/l; D-glucose 1 g/l) for example and concentration by ultrafiltration until a hemoglobin concentration of about 7% is obtained.

Preparations of macromolecular conjugates of hemoglobin obtained according to the invention have been examined as potential transporters of oxygen. It has been possible to show that they are in fact capable of binding oxygen reversibly and, in particular, of releasing it more readily than free hemoglobin as is illustrated by the curves relating to the oxygen affinity of the products described in the Examples 1, 3 and 5 below and presented in FIG. 5 which will be discussed later. In fact, these preparations appear to be characterized by half-saturation pressures ($P_{50}$) which are very high (from 900 to 5,000 Pa) whereas under the same conditions (0.05M NaCl, pH 7, 25° C.) that of native hemoglobin is equal to about 480 Pa.

Thus, these conjugates can be used to supply large amounts of oxygen to ischemic tissues. They may also be used in transfusions and be administered to patients in the form of an aqueous solution made isotonic with blood, in the presence or absence of excipients. The conjugates can also be lyophilized in the presence or absence of a protecting agent or atomized and be redissolved in water before utilization.

The invention will be better understood with the aid of the examples which follow and which are not intended to be limiting in scope.

EXAMPLE 1

Synthesis of a covalently linked conjugate of hemoglobin and dextran sulfate (molecular weight of the dextran: 40,000)

The sodium salt of dextran sulfate containing 8% sulfur (corresponding to about 5.4 moles of sulfate ions per 10 moles of glucopyranose) is prepared from dextran having a mean molecular weight of 40,000 (Pharmacia, Uppsala, Sweden), as indicated in C. R. RICKETTS, Biochem. J. 1952, 51, 129.

The activation of this dextran sulfate is carried out by periodate oxidation as indicated in E. DELLACHERIE et al., Biochem. Biophys. Acta 1983, 749, 106. The quantity of $NaIO_4$ used is such that the dextran sulfate dialdehyde contains about 18 aldehyde groups per 100 glucopyranose units. This compound is dialyzed extensively against water, then lyophilized and stored in the cold in a vacuum.

10 g of this dextran sulfate dialdehyde are dissolved in 100 ml of a 20% NaCl solution and the solution is deoxygenated in a glove box placed under vacuum, then nitrogen is bubbled through, this operation being repeated three times. 120 ml of a 9% hemoglobin solution which has been deoxygenated by the same procedure is added and the pH of the resulting mixture is adjusted to 7.5 by the addition of deoxygenated 0.1N sodium hydroxide solution. The solution is maintained at 25° C. without stirring and reaction is allowed to proceed for 6 hours.

3.5 ml of a freshly made solution of 200 mg of NaBH$_4$ in 5 ml of $10^{-3}$M NaOH are then added. The reaction is allowed to proceed for 1 h, then the pH is lowered to 7 in order to destroy excess reducing agent.

Figure 2:
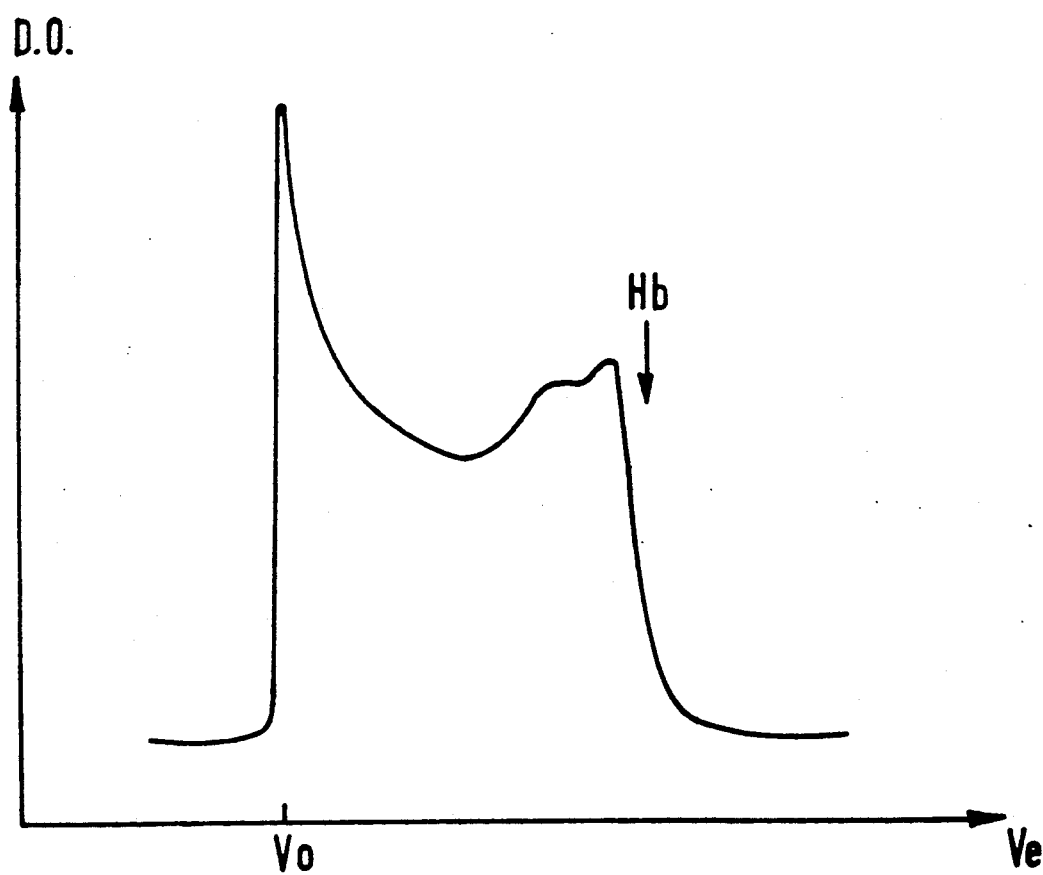
FIG. 2 graphically illustrates the variation of the optical density as a function of the elution volume for the conjugate of Example 1.

Examination of the chromatogram obtained after filtration through a column of gel of the type TSK SW 3,000 Beckman (zone of exclusion 300,000 daltons) shows that very little unbound hemoglobin remains. Reference may be made to FIG. 2, in which is shown the variation of the optical density as a function of the elution volume and which shows that the peak corresponding to unbound hemoglobin is very small.

Figure 5:
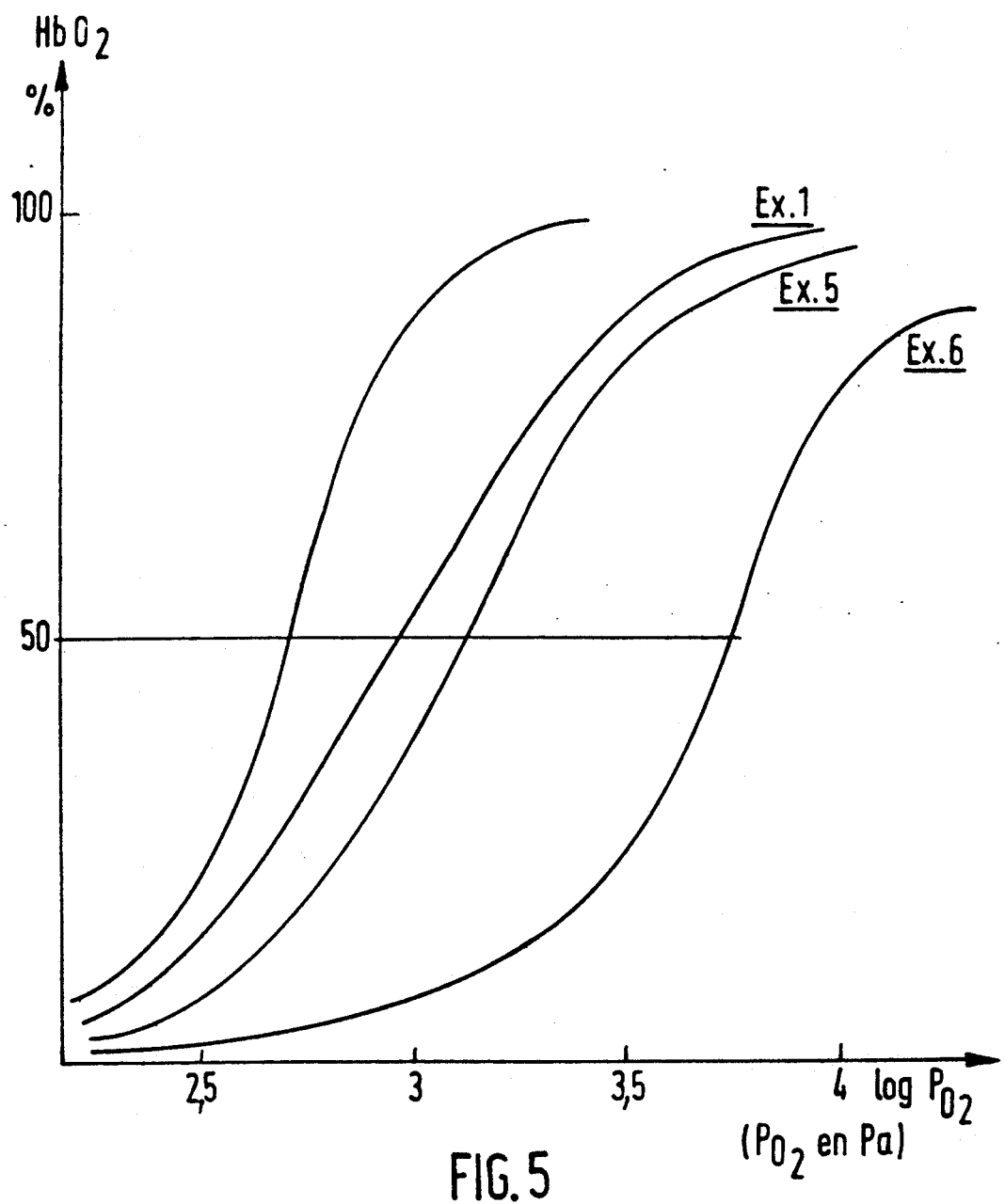
FIG. 5 shows oxygen affinity curves for free hemoglobin and the conjugates according to Examples 1, 4 and 6.

The curve showing the oxygen affinity of this conjugate of the invention is presented in FIG. 5 and the curve for the oxygen affinity of free hemoglobin is shown as a dotted line.

The P$_{50}$ is about 850 Pa (25° C., 0.05M NaCl, pH 7).

The proportion of methemoglobin is about 5%. This amount is measured as indicated in EVELYN, K. A. and MALLOY, H. I., J. Biol. Chem. 1938, 126, 655.

EXAMPLE 2

Synthesis of a covalently linked conjugate of hemoglobin and dextran sulfate (molecular weight of the dextran = 10,000).

1) Preparation of the above-mentioned conjugate according to the invention

The reaction is carried out between deoxyhemoglobin and the sodium salt of dextran sulfate dialdehyde prepared according to the method described in Example 1 from dextran of molecular weight of about 10,000 and containing 12% sulfur (corresponding to 9.8 sulfate ions per 10 glucopyranose units) and 14 aldehyde groups per 100 glucosidic units.

10 g of dextran sulfate dialdehyde and 120 ml of a 9% deoxyhemoglobin solution are allowed to react for 7 hours at 25° C. in the total absence of oxygen (same conditions as for the reaction described in Example 1) and all of the hemoglobin becomes bound to the polymer and the P$_{50}$ of the conjugate is about 1,060 Pa (25° C., 0.05M NaCl, pH 7).

2) Comparison between a mixture of hemoglobin and dextran sulfate and a covalently linked conjugate according to the invention of hemoglobin and dextran sulfate prepared as in 1

It has been verified by steric exclusion chromatography that a mixture of dextran sulfate (a very good macromolecular effector of hemoglobin and which thus associates very strongly with deoxyhemoglobin) and oxygenated hemoglobin is eluted from the chromatography column as two separate peaks corresponding to free hemoglobin and free dextran sulfate, respectively.

Figure 6:
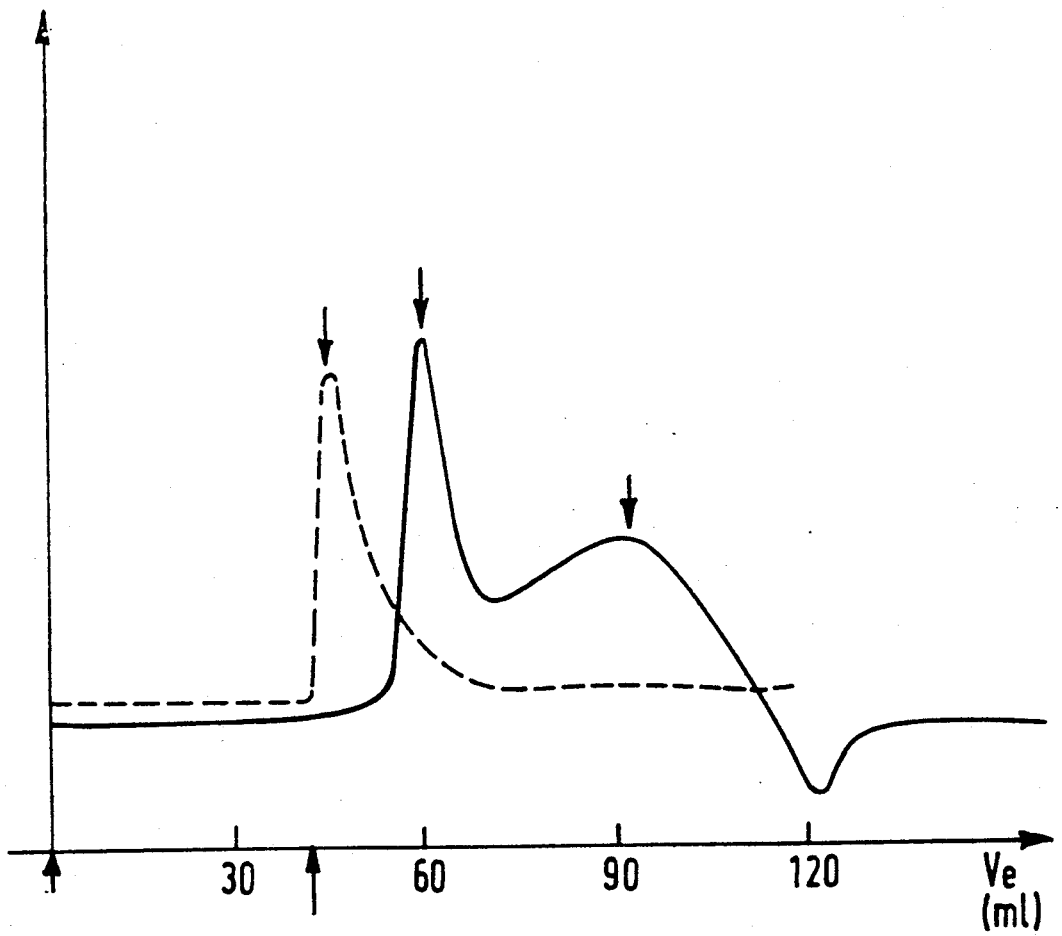
FIG. 6 shows the variation of the refractive index as a function of the elution volume of free hemoglobin and free dextran sulfate and the conjugate of Example 2.

Reference may be made to FIG. 6 in which is shown the variation of the refractive index (along the ordinate) as a function of the elution volume (along the abscissa) subsequent to the injection of a mixture of dextran sulfate/hemoglobin. The curve obtained is represented by a continuous line and it shows two peaks, the first of which (elution volume of about 60 ml) corresponds to free hemoglobin and the second (elution volume of about 90 ml) corresponds to free dextran sulfate.

FIG. 6 also presents a dotted curve corresponding to the injection of the covalently linked conjugate of dextran sulfate/hemoglobin in conformity with the invention, the synthesis of which was outlined above in 1). This curve comprises only a single elution peak (for which the volume along the abscissa corresponds to the exclusion volume) corresponding to a molecular weight higher than those of free hemoglobin and free dextran sulfate.

The separation giving rise to these two curves was performed on a 55 cm column of Ultrogel AcA 54, IBF (zone of exclusion 90,000) under the following conditions: 0.05M Tris buffer; 0.15M NaCl; pH 7.2; flow rate 30 ml/h.

From this it will be deduced that it is necessary to bind the ligand-polymer to the hemoglobin in an irreversible manner such that:

a) the effector groups of the polymer always remain close to the hemoglobin molecule so that they can exercise their role as modulators of hemoglobin as soon as the latter has liberated its bound oxygen;

b) the polymer and hemoglobin by remaining associated with each other can be retained within the vascular circulation.

It is also to be observed that the affinity for O$_2$ of the hemoglobin thus bound covalently is not increased compared with that of free hemoglobin and in some cases—especially when dextran polycarboxylates (dextran benzene hexacarboxylate, dextran polyacrylate) are used as polymeric effectors—it has even been recorded that the P$_{50}$ of hemoglobin after coupling to the polymer was higher than that of free hemoglobin in the presence of the same polymer but before it was coupled to it.

Thus it can be deduced that the conjugates of the invention in which the polymers are coupled covalently, hence irreversibly, to the hemoglobin molecule are such that the hemoglobin exhibits an enhanced functional activity after immobilization since the hemoglobin is in the deoxygenated form during the chemical reaction and in this form some chemical functions are masked which prevent them from being affected by the coupling reaction.

EXAMPLE 3

Synthesis of a covalently linked conjugate of hemoglobin and dextran sulfate (molecular weight of the dextran = 6,000).

The reaction is carried out between deoxyhemoglobin and the sodium salt of dextran sulfate dialdehyde prepared according to the method described in Example 1 from dextran having a molecular weight of about 6,000, and containing 3% sulfur (corresponding to 1.7 sulfate ions per 10 glucopyranose units) and 18 aldehyde groups per 100 glucosidic units. 10 g of dextran sulfate dialdehyde and 120 ml of a 9% deoxyhemoglobin solution are allowed to react for 6 hours at 25° C. in the total absence of oxygen (same conditions as for the reaction described in Example 1) and all of the hemoglobin becomes bound to the polymer and the P$_{50}$ of the conjugate is about 602 Pa (25° C., 0.05M NaCl, pH 7).

EXAMPLE 4

Synthesis of a covalently linked conjugate of hemoglobin and dextran phosphate (molecular weight of the dextran = 40,000).

The sodium salt of dextran phosphate containing 12% phosphorus (corresponding to about 12 moles of phosphate ions per 10 moles of glucopyranose) is prepared from dextran of molecular weight = 40,000 as indicated in G. DAUL et al., Industrial and Engineering Chemistry, 1954, 46, 1042.

This dextran phosphate is activated by periodate oxidation as described in Example 1 so as to generate about 18 aldehyde groups per 100 glucosidic units.

This dextran phosphate dialdehyde is allowed to react with deoxyhemoglobin in proportions and under conditions completely identical with those described in Example 1. After 6 hours of reaction, followed by reduction using NaBH$_4$ as indicated in Example 1, all of the hemoglobin is bound. The curve relating to the oxygen affinity of this conjugate is shown in FIG. 5.

The P$_{50}$ of the conjugate is about 1240 Pa (25° C., 0.05M NaCl, pH 7). The proportion of methemoglobin is of the order of 4%.

EXAMPLE 5

Synthesis of a covalently linked conjugate of hemoglobin and dextran polycarboxylate (molecular weight of the dextran = 40,000).

1st method

Aminated dextran containing $5 \times 10^{-4}$ moles of NH$_2$ per g of dry product (corresponding to 8 moles of NH$_2$ per 100 moles of glucopyranose) is prepared according to P. HUBERT et al., Proc. Natl. Acad. Sci. USA 1978, 75, 3143, by the action of ammonia on dextran activated by epichlorohydrin.

1 g of this aminated dextran is dissolved in 20 ml of water and the pH is adjusted to 6.5 with 0.1N HCl. 1.7 g of benzene hexacarboxylic acid are then added, followed by 1 g of 1-ethyl-3-(3-dimethylaminopropyl) carbodiimide hydrochloride (EDCI). The pH is brought to 6.5 and the reaction is allowed to proceed for 3 days at 20° C. After being dialyzed against a solution of 0.5M sodium acetate, the mixture is treated with acetic anhydride in order to block the unsubstituted amine functions of the dextran. Contaminants of low molecular weight are then removed by desalting the solution on a column of Ultrogel AcA 202 (IBF-France) in 0.2M phosphate buffer, pH 7.2.

After being extensively dialyzed against water, the solution containing the polyanionic polymer is lyophilized. The compound is stored in the cold in a vacuum.

Figure 3:
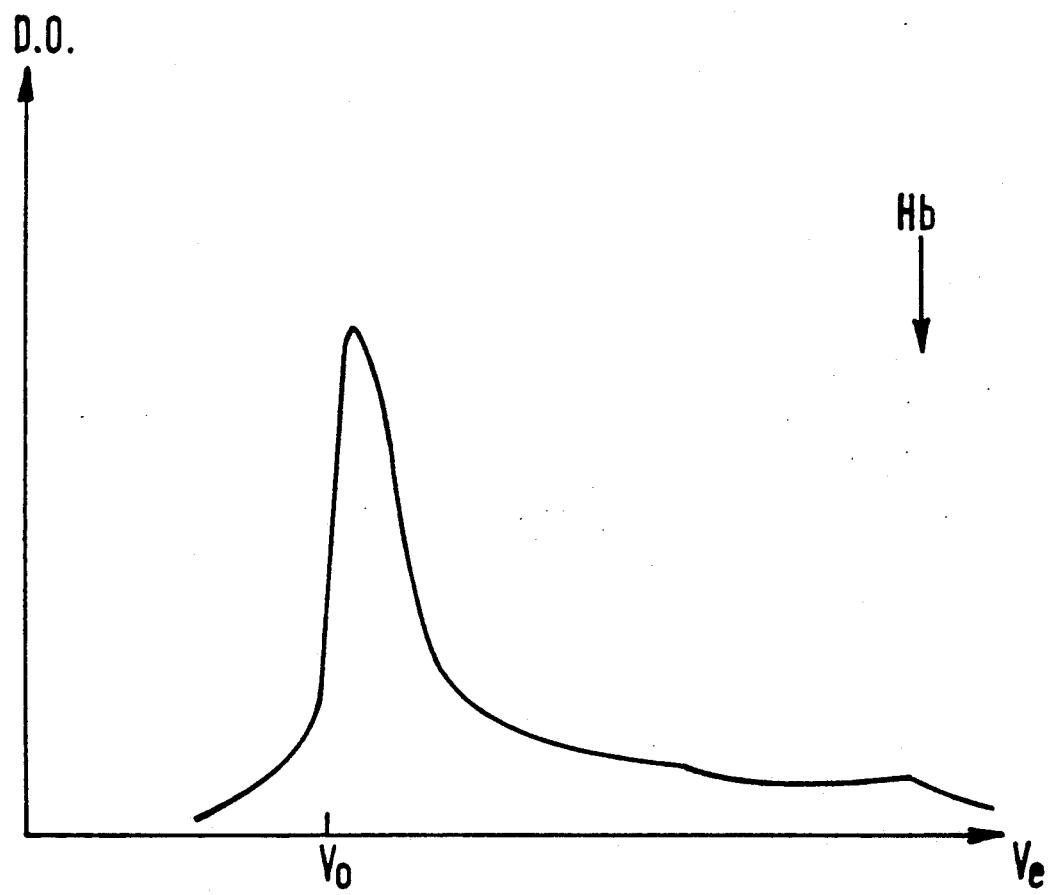
FIG. 3 shows the variation of the optical density as a function of the elution volume of the conjugate of Example 5.

0.5 g of this dextran polycarboxylate are dissolved in 25 ml of 0.05M aqueous NaCl solution. The pH is brought to 6.5 with 0.1N sodium hydroxide and the solution is deoxygenated as indicated in Example 1. 15 ml of a 10% hemoglobin solution, which had been deoxygenated under the same conditions, are then added. To the mixture, kept in a glove box and with nitrogen bubbling through, 60 mg of EDCI are then added and the reaction is allowed to proceed for 10 hours at 20° C. The chromatogram obtained after filtration through a column of Ultrogel AcA 34 (IBF-France) confirms the absence of free hemoglobin. Reference may be made to FIG. 3 in which is shown the variation of the optical density as a function of elution volume and which indicates that the peak corresponding to unbound hemoglobin is very small. The P$_{50}$ of the conjugate is about 1360 Pa (25° C., 0.05M NaCl, pH 7).

EXAMPLE 6

Synthesis of a covalently linked conjugate of hemoglobin and dextran polycarbonate (molecular weight of the dextran: 40,000).

2nd method

Dextran polycarboxylate containing oligomeric chains of acrylic acid is prepared by generating along the length of the polysaccharide chain radicals which serve to initiate the oligomerization of acrylic acid in aqueous medium. The sodium salt of this dextran polycarboxylate is purified by extensive dialysis against water, then lyophilized.

1 g of the sodium salt of this dextran polycarboxylate containing, on average, one dicarboxylic acid chain per glucosidic unit, is allowed to react with deoxyhemoglobin under conditions completely identical with those which are described in Example 5.

Figure 4:
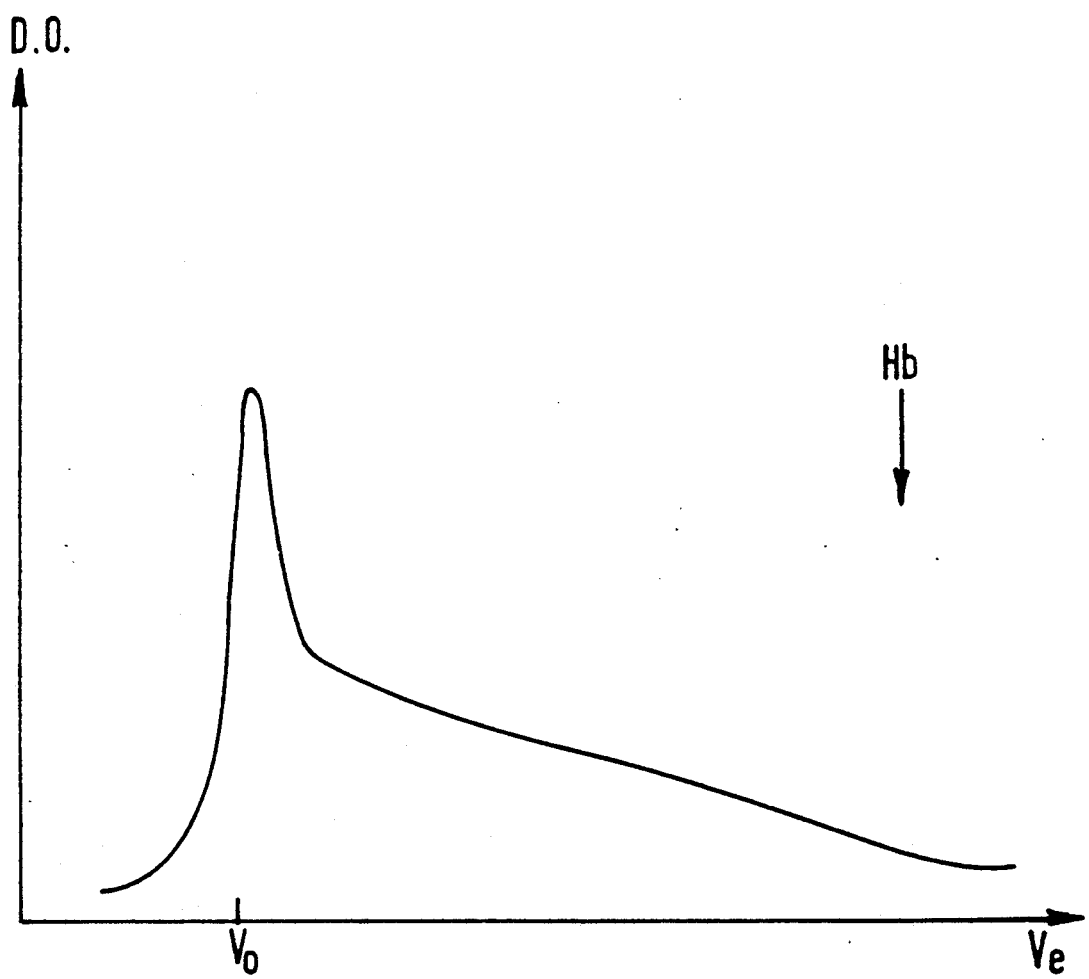
FIG. 4 graphically illustrates the variation of the optical density as a function of the elution volume of the conjugate of Example 6.

The reaction is stopped after 4 hours and the mixture is chromatographed on a column of Ultrogel AcA 34 (IBF-France), a step which confirms that no free hemoglobin remains. Reference may be made to FIG. 4, in which is shown the variation of the optical density as a function of elution volume and which indicates that the peak corresponding to unbound hemoglobin is very small.

The curve showing the affinity of this conjugate for oxygen is presented in FIG. 5. The P$_{50}$ is about 5,500 Pa (25° C., 0.05M NaCl, pH 7).

Assays of Acute Toxicity in Animals

The various polyanionic polymers described in the examples have been injected into mice of the SWISS strain under the following conditions: the polymers were dissolved in distilled water at a concentration lying between 2.5 g and 5 g/l and the pH is adjusted to 7.4. 0.5 ml of each solution were then injected by the intraperitoneal route into 5 mice, whose behaviour was then kept under observation for a period of 7 days. These assays have not revealed any symptoms of acute toxicity.

We claim:
1. A conjugate comprising:
    a hemoglobin which can undergo a reversible transition between an oxygenated state and a deoxygenated state: and
    a water-soluble hemocompatible polymer covalently bonded to the hemoglobin, ionically bonded to the hemoglobin and having a molecular weight of about 1,000 to 500,000 daltons, wherein the polymer has a chemically bonded ligand with at least one negative charge borne by an anionic group which forms an ionic bond with an amino group at an allosteric site on the hemoglobin, the anionic group of the ligand comprising a sulfate, phosphate or carboxylate moiety, and wherein further the polymer or ligand has a polar group which forms a covalent bond between the polymer and the hemoglobin, the polar group comprising a hydroxyl, carboxyl, amino or aldehyde moiety;
    the conjugate having a mean molecular weight of about 70,000 to 1,000,000 daltons, and wherein salt bridges between internal NH$_3^+$ and COO$^-$ groups of the hemoglobin are intact when the hemoglobin is in the deoxygenated state.
2. The conjugate of claim 1 having a mean molecular weight of about 70,000 to 500,000 daltons.
3. The conjugate of claim 2, wherein the polymer has a molecular weight of about 1,000 to 100,000 daltons.
4. The conjugate of claim 2, wherein the polymer has a molecular weight of less than 10,000 daltons.

5. The conjugate of claim 1, wherein the polar group is on the polymer.

6. The conjugate of claim 1 which can comprise a plurality of the ligands on the polymer and wherein:

when each ligand has chemically bound an anionic group which comprises a sulfate or phosphate moiety, there is at least one ligand for every ten monomers of the polymer;

when at least one of the ligands has chemically bound at least two anionic groups which comprise a sulfate and/or phosphate moiety, there is as few as one ligand on the polymer;

when each ligan has chemically bound negative charges borne by carboxylate moieties, there are at least two carboxylate moieties on each ligand and there is at least one ligand for every five monomers; and when at least one of the ligands has chemically bound at least three negative charges which are borne by carboxylate moieties, there is at least one ligand on the polymer.

7. The conjugate of claim 1, wherein the polymer is a polysaccharide, polyvinyl alcohol, polyvinylpyrrolidone, polymethacrylate, polypeptide or polyalkylene glycol.

8. The conjugate of claim 7, wherein the polymer is a hydroxylalkyl starch in which the alkyl is of 2 to 4 carbon atoms inulin, dextran, an aminated dextran, or a polyalkylene glycol in which the alkene is of 2 to 5 carbon atoms.

9. The conjugate of claim 7, wherein the polymer is a dextran having a mean molecular weight of no more than 70,000 daltons or is a polyalkylene glycol, polyvinylpyrrolidone or polymethacrylate having a mean molecular weight of no more than 10,000 daltons.

10. The conjugate of claim 1, wherein the ligand is chemically bound to the polymer by an ester, ether, amide or amine linkage.

11. The conjugate of claim 1, wherein the ligand is: a $-OSO_3H$, $-OPO_3H_2$,

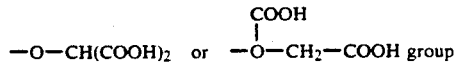

or a pyridoxal sulfate, epinephrine disulfate, epinephrine trisulfate, norepinephrine disulfate, norepinephrine trisulfate, phenolphthalein disulfate, pyridoxal phosphate, adenosine triphosphate, phosphotyrosine, phosphoserine or inositol (tri-,tetra-,penta- or hexa-) phosphate group; or a polycarboxylic acid group containing from 2 to 10 carbon atoms; or a benzene carboxylic acid group comprising at least two carboxylic acid functions; or a 2,3-diphosphoglycerate, citrate, 1,2,3-propane tricarboxylate or butane tetra-carboxylate group; or a group of the formula:

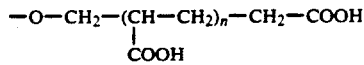

in which n is an integer of 1 to 4.

12. The conjugate of claim 1, wherein the polar group and the ligand constitute a unitary group on the polymer that is covalently and ionically bonded to the hemoglobin.

13. The conjugate of claim 12, wherein the unitary group comprises: 1) an anionic group with a sulfate, phosphate or carboxylate moiety forming an ionic bond with an allosteric amino group of the hemoglobin; and 2) a polar group with an aldehyde, carboxyl or hydroxyl moiety forming a covalent bond with an amino group of the hemoglobin.

14. The conjugate of claim 1, wherein the polymer is a dextran having a mean molecular weight of about 40,000 daltons, containing about 5.4 or 12 moles of $-OS_3H$ groups per 10 glucopyranose moieties, and having covalent bonds between the polymer and the hemoglobin resulting from bonding between about 18 aldehyde groups per 100 glucosidic units on the dextran and $NH_2$ groups of the hemoglobin.

15. The conjugate of claim 1, wherein the polymer is a dextran having a mean molecular weight of about 10,000 daltons, containing about 9.8 moles of $-OSO_3H$ groups per 10 glucopyranose moieties, and having covalent bonds between the polymer and the hemoglobin resulting from bonding between about 14 aldehyde groups per 100 glucosidic units on the dextran and $NH_2$ groups of the hemoglobin.

16. The conjugate of claim 1, wherein the polymer is a dextran having a mean molecular weight of about 6,000 daltons, containing about 1.7 $-OSO_3H$ groups per 10 glucopyranose moieties, and having covalent bonds between the polymer and the hemoglobin resulting from bonding between about 18 aldehyde groups per 100 glycosidic units on the dextran and $NH_2$ groups of the hemoglobin.

17. The conjugate of claim 1, wherein the polymer is an aminated dextran having a mean molecular weight of about 40,000 daltons and ionic bonds are formed by means of a plurality of carboxylate groups of benzene hexacarboxylic acid moieties on the polymer and $NH_2$ groups of the hemoglobin.

18. The conjugate of claim 1, wherein the polymer is a polycarboxylated dextran having a mean molecular weight of about 40,000 daltons and about one dicarboxylic acid per glycopyranose moiety, and covalent and ionic bonds are formed between $NH_2$ groups on the hemoglobin and different carboxylic acid groups on the polymer.

19. A process for making a conjugate of claim 1, comprising the steps of:
a) providing the polymer which can covalently bond to a hemoglobin and which can also ionically bond to a hemoglobin; and then
b) reacting the polymer with a deoxygenated hemoglobin in a aqueous medium at a pH of about 5 to 9 to form simultaneously an ionic bond and a covalent bond between the hemoglobin and the polymer without denaturing the hemoglobin.

20. The process of claim 19, wherein amine groups on the conjugate are subsequently stabilized by being reduced to amine groups.

21. The process of claim 20, wherein imine groups are reduced with $NaBH_4$, $NaCNBH_3$, dimethylaminoborane or $HCOO_4$.

22. The process of claim 19, wherein before step a), the polymer is sulfated, phosphorylated or carboxymethylated to provide the ligand with the anionic group on the polymer.

23. The process of claim 22, wherein before step a), the polymer is activated by coverting an hydroxy group thereon into an aldehyde group.

24. The process of claim 23, wherein the hydroxy group is converted to an aldehyde group by a periodate oxidation.

25. The process of claim 19, wherein step b) is carried out for a length of time such that no more than 5% methemoglobin is formed.

26. The process of claim 19, wherein step b) is carried out between about 3° and 30° C.

27. The conjugate of claim 8 wherein the polymer is polyethylene glycol or polypropylene glycol.

28. The conjugate of claim 1, wherein the polar group is on the ligand.

29. The conjugate of claim 1, wherein the polar group comprises a hydroxyl, carboxyl or aldehyde moiety which forms a covalent bond with an amino group on the hemoglobin.

* * * * *

UNITED STATES PATENT AND TRADEMARK OFFICE
CERTIFICATE OF CORRECTION

PATENT NO. : 5,079,337
DATED : January 7, 1992
INVENTOR(S) : LEONARD et al.

It is certified that error appears in the above-identified patent and that said Letters Patent is hereby corrected as shown below:

On the title page:

Section [75] "Inventors:", after "Pierre Labrude, Laxou" insert the following two additional inventors -- Francois Bonneaux, Nancy; Daniel Sacco, Nancy, --.

Signed and Sealed this

First Day of June, 1993

Attest:

MICHAEL K. KIRK

Attesting Officer

Acting Commissioner of Patents and Trademarks